US00PP22601P2

(12) United States Plant Patent
Probst

(10) Patent No.: US PP22,601 P2
(45) Date of Patent: Mar. 20, 2012

(54) ***COREOPSIS* PLANT NAMED 'COSMIC EYE'**

(50) Latin Name: ***Coreopsis* hybrid**
Varietal Denomination: Cosmic Eye

(76) Inventor: Darrell R. Probst, Hubbardston, MA (US)

( * ) Notice: Subject to any disclaimer, the term of this patent is extended or adjusted under 35 U.S.C. 154(b) by 273 days.

(21) Appl. No.: 12/657,956

(22) Filed: Jan. 29, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Wendy C Haas
(74) *Attorney, Agent, or Firm* — Penny J. Aguirre

(57) ABSTRACT

A new cultivar of hybrid *Coreopsis* named 'Cosmic Eye' characterized its large inflorescences with ray florets that are bright yellow in color with sharply contrasting bright red eye zones, its low growing and compact plant habit with flowers held well above the foliage, and its perennial habit and cold hardiness to at least U.S.D.A. Zone 5.

2 Drawing Sheets

Botanical classification: *Coreopsis* hybrid.
Variety denomination: 'Cosmic Eye'.

CROSS REFERENCE TO A RELATED APPLICATION

This application is co-pending with a U.S. Plant Patent Application filed for a plant derived from the same cross in the Inventor's breeding program that is entitled *Coreopsis* Plant Named 'Galaxy' (U.S. Plant Pat. No. 21,999).

BACKGROUND OF THE INVENTION

The present invention relates to a new and distinct cultivar of *Coreopsis* plant, botanically of hybrid origin and known as *Coreopsis* 'Cosmic Eye' and will be referred to hereinafter by its cultivar name, 'Cosmic Eye'. The new cultivar of *Coreopsis* is an herbaceous perennial grown for landscape and container use.

The new Invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A Zone 5 in a wide range of flower colors and plant forms. The Inventor collected seed in the wild from five different species that are not commercialized and made six generations of crosses to produced interspecific hybrids to utilize in his breeding work.

The Inventor made a controlled cross in September of 2006 in his test garden in Hubbardston, Mass. between an unnamed sibling of *Coreopsis* 'Redshift' (U.S. Plant Pat. No. 20,412) as the female parent and an unnamed sibling of *Coreopsis* 'Full Moon' (U.S. Plant Pat. No. 19,364) as the male parent. 'Cosmic Eye' was selected in summer 2007 as a single unique plant amongst the resulting seedlings.

Asexual reproduction of the new cultivar was first accomplished by stem cuttings in Hubbardston, Mass. in August of 2007 by the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Cosmic Eye' as unique from all *Coreopsis* cultivars and species known to the Inventor.

1. 'Cosmic Eye' exhibits a very low growing, compact plant habit; reaching about 12 inches (30 cm) in height in bloom.
2. 'Cosmic Eye' exhibits foliage that branches low to the ground with flowers held well above the foliage.
3. 'Cosmic Eye' exhibits large inflorescences with ray florets that are bright yellow in color with sharply contrasting bright red eye zones.
4. 'Cosmic Eye' exhibits a reliable perennial habit and is cold hardy at least to U.S.D.A. Zone 5.

'Cosmic Eye' differs from its female parent in that the female parent has a much taller plant height, reaching 3 feet in height, and in having flowers with ray florets that are pale yellow in color with red streaks. The male parent differs from 'Cosmic Eye' in being taller in plant height, reaching about 2 feet in height, and in having flowers with ray florets that are solid light yellow in color. 'Cosmic Eye' can be compared to *Coreopsis* cultivars 'Redshift' and 'Full Moon'. 'Redshift' is similar to 'Cosmic Eye' in having flowers with ray florets that are yellow with a red eye zone, however 'Redshift' differs from 'Cosmic Eye' in being taller in plant height and in having ray florets that change in color to almost solid red late in the season when temperatures are cooler. 'Full Moon' differs from 'Cosmic Eye' in being taller in plant height and in having flowers with ray florets that are solid yellow in color and lack eye zone coloration.

BRIEF DESCRIPTION OF THE DRAWING

The accompanying colored photographs illustrate the overall appearance and distinct characteristics of the new *Coreopsis*. The photographs were taken of a two year-old plant of 'Cosmic Eye' as grown in a garden in Mount Vernon, Wash.

The photograph in FIG. 1 shows the overall growth and flowering habit of 'Cosmic Eye'.

Figure 1:
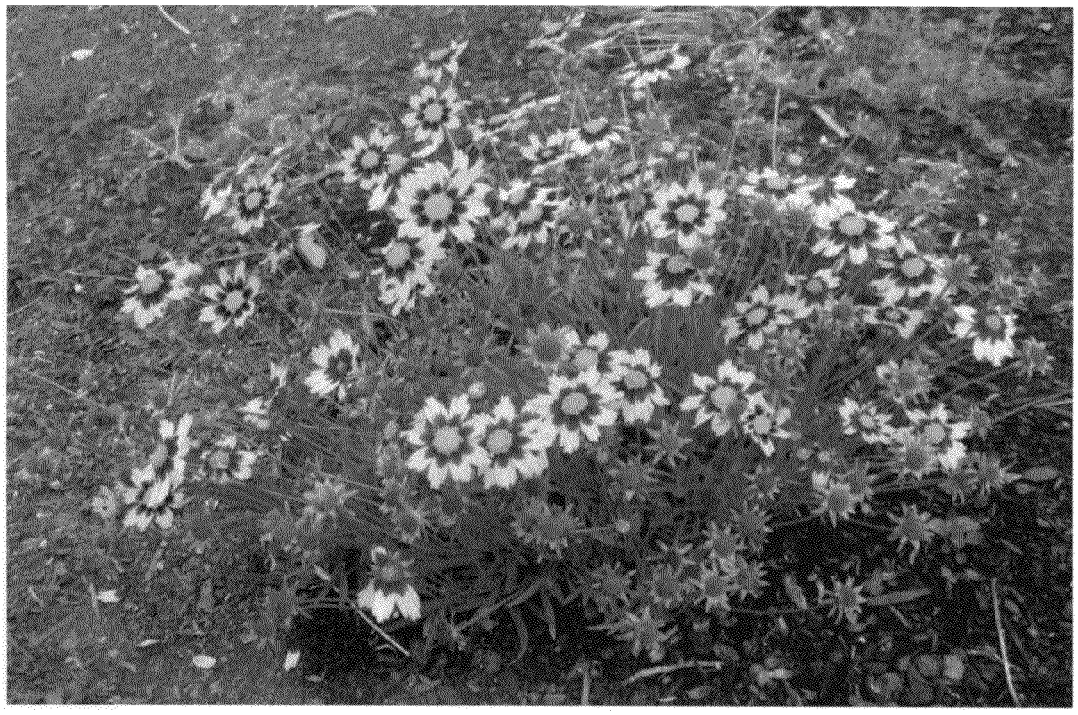
Figure 2:
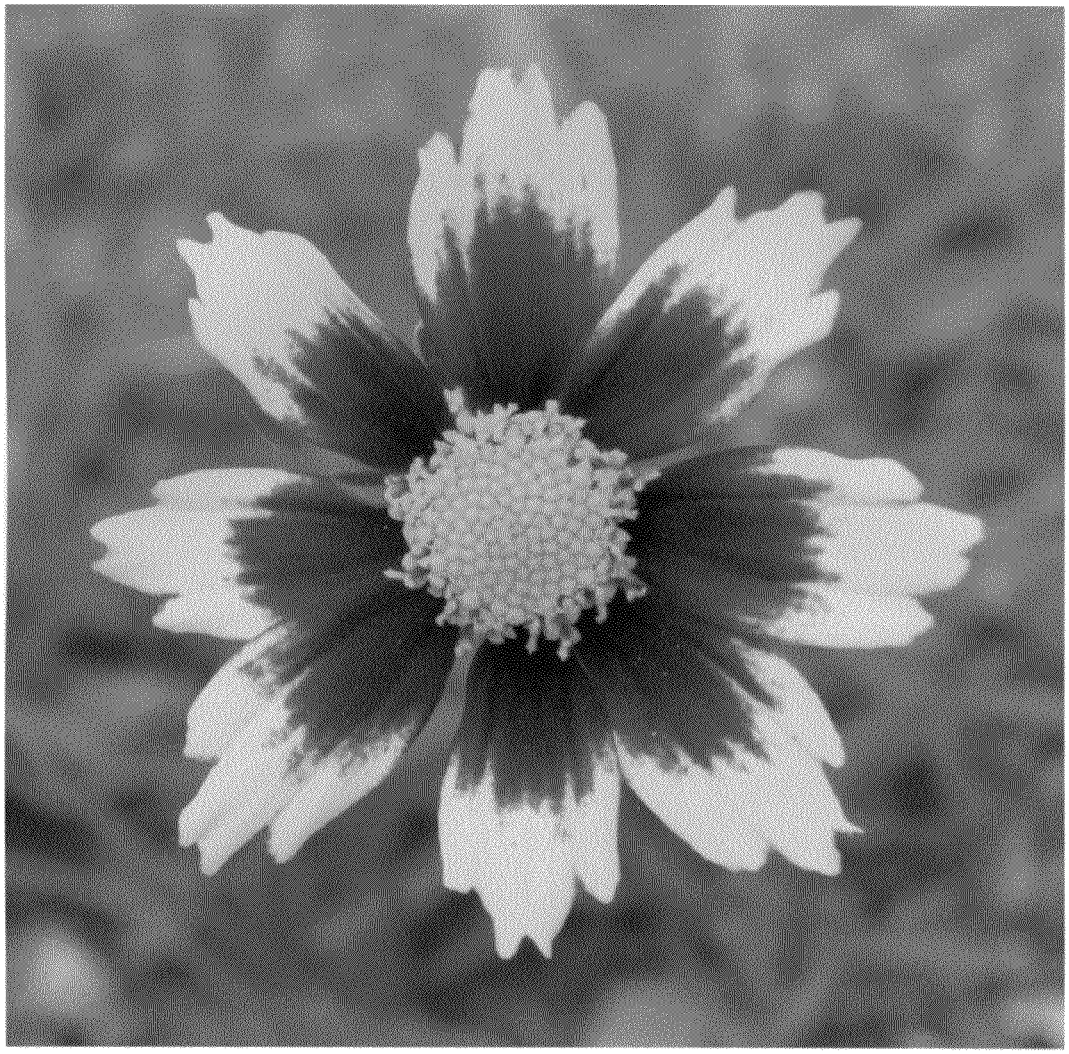

The photograph in FIG. 2 provides a close-up view of an inflorescence of 'Cosmic Eye'. The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for two years in a trail garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from June until frost in central Massachusetts.

*Plant habit*.—Herbaceous perennial, clump-forming, compact, low growing leafy stems with flowering stem held above the foliage.

*Height and spread*.—Reaches 10 to 15 cm (4 to 6 inches) in height with blooms reaching about 24 cm (12 inches) in height, spreads to about 24 cm (12 inches).

*Cold hardiness*.—At least to U.S.D.A Zone 5.

*Diseases resistance*.—Relatively disease resistant with no particular resistance to specific diseases observed.

*Root description*.—Fibrous, fine and well-branched.

Growth and propagation:

*Propagation*.—Terminal stem cuttings and division.

*Growth rate*.—Vigorous but retaining a compact habit.

Stem description:

*Shape*.—Oval, solid.

*Stem color*.—144A.

*Stem size*.—Main stem (including peduncles) averages 23 cm in length and 4 mm in width with lateral branches an average of 6 cm in length and 2 mm in width.

*Stem surface*.—Glabrous when young, ridged and sparsely covered with minute translucent hairs when mature.

*Branching habit*.—An average of 7 basal branches with 6 secondary branches, branch internode is variable but typically about 3 cm and arise opposite at nodes.

Foliage description:

*Leaf division*.—Simple.

*Leaf margins*.—Entire to tri-lobed, covered with short hairs and slight undulations.

*Leaf size*.—Variable, an average of 7 cm in length and width when mature with center lobe an average of 7 mm in length and 5 mm in width and secondary lobes an average of 3 cm in length and 4 mm in width.

*Leaf shape*.—Lanceolate with lanceolate lobes when tri-fid.

*Leaf base*.—Attenuate.

*Leaf apex*.—Narrowly acute.

*Leaf venation*.—Pinnate, not prominent, coloration same as leaf on both surfaces.

*Leaf attachment*.—Sessile.

*Leaf arrangement*.—Opposite.

*Leaf surface*.—Dull and very finely puberulent on upper surface and lower surface.

*Leaf color*.—Young and mature upper surface; N137B, young and mature lower surface; 137B.

Flower description:

*Inflorescence type*.—Composite with ray florets surrounding disk florets in the center, forming a radiant head, inflorescences are borne on terminals arising from leaf axils.

*Lastingness of inflorescence*.—About 8 to 10 days until senescence of ray flowers, bracts and disk flowers are persistent.

*Fragrance*.—Faint.

*Quantity of inflorescences*.—An average of 6 per lateral branch, an average of 60 per plant grown in a one-gallon container.

*Inflorescence size*.—Up to 1.3 cm in depth and up to 4.6 cm in diameter with disk portion up to 1.2 cm in diameter.

*Inflorescence buds*.—Average of 9 mm in depth and diameter, shape is spherical, color is 17C surrounded with bracts 137B in color.

*Peduncle*.—Strong, average of 9 cm in length and 1.5 mm in diameter, 144A in color, glabrous surface.

Involucral bracts:

*Bract number*.—Two rows of 7.

*Bract arrangement*.—Outer bracts are un-fused and somewhat reflexed when flower is fully open and becoming horizontal after ray florets drop, inner bracts overlap and surround receptacle with a campanulate form with apical portion un-fused, spreading, and held close to ray florets.

*Bract size*.—Outer bracts; up to 1 cm in length and 2.5 mm in width, inner bracts; up to 9 mm in length and 3.5 mm in width with free portion an average of 4 mm in length and 3.5 mm in width.

*Bract color*.—Outer bracts; 137A on both surfaces, inner bracts; fused portion 146A, un-fused portion 146C in center with apex and margin 144C.

*Bract texture*.—Outer bract; puberulent, inner bracts waxy.

*Bract apex*.—Outer bract; acute, inner bracts; acute.

*Bract base*.—Truncate.

*Bract margins*.—Entire with fine short hairs on outer bracts.

*Bract shape*.—Outer bracts; lanceolate, inner bracts; free portion broadly lanceolate.

Ray florets (pistillate):

*Number*.—7.

*Shape*.—Oblanceolate, appearance of three longitudinal sections with center section longer and apex of each free.

*Size*.—Up to 2 cm in length and 1 cm in width.

*Apex*.—3-lobed with center lobe emarginate and side lobes rounded.

*Base*.—Broadly cuneate.

*Margins*.—Entire on sides, lobed at apex.

*Aspect*.—Held slightly cupped upward.

*Texture*.—Velvety on upper surface and glabrous on lower surfaces.

*Color*.—Upper surface when opening and mature; 5A with eye zone (lower one-half of petal) 187A, lower surface when opening and mature; 5B with eye zone (lower one-half of petal) slightly suffused and with a few stripes of 187B.

Disk flowers (perfect):

*Shape*.—Tubular, corolla is fused, flared at apex.

*Size*.—About 6 mm in length and 1.3 mm in width.

*Color*.—En masse; 153A when immature, 17A when fully open and becoming a blend of 200C and 200D when dried and ray florets drop, corolla; base (tube) is 2C in color, flared portion is 17A and translucent.

*Receptacle*.—About 3.5 mm in diameter and 2 mm in depth, 1D in color.

Reproductive organs:

*Presence*.—Disk flowers are perfect, ray flowers are pistillate.

*Gynoecium*.—1 Pistil, 5 mm in length, style is very fine and about 151C in color and translucent, bifid pilose stigma is 17A in color with branches about 1 mm in length and recurved, ovary is 1.5 mm in length, 1 mm in width, inferior, and 145B suffused with 187A in color.

*Androcoecium*.—5 stamens, fused into tube surrounding style, 3 mm in length and 0.7 mm in width, about 165A in color, no pollen was observed.

*Fruit/seed*.—No fruit or seed development was observed.

It is claimed:

1. A new and distinct cultivar of *Coreopsis* plant named 'Cosmic Eye' as herein illustrated and described.

* * * * *